US005783178A

United States Patent [19]
Kabanov et al.

[11] Patent Number: 5,783,178
[45] Date of Patent: Jul. 21, 1998

[54] POLYMER LINKED BIOLOGICAL AGENTS

[75] Inventors: Alexander Victorovich Kabanov, Omaha, Nebr.; Valery Yulievich Alakhov, D'Urfe, Canada

[73] Assignee: Supratek Pharma, Inc., Montreal, Canada

[21] Appl. No.: 342,079

[22] Filed: Nov. 18, 1994

[51] Int. Cl.$^6$ .................................................. A61K 31/74
[52] U.S. Cl. .................................. 424/78.31; 424/78.08; 424/78.31
[58] Field of Search ........................... 536/6.4, 16.8, 536/18.1; 424/78.08, 78.31, 78.37

[56] References Cited

U.S. PATENT DOCUMENTS

| | | | |
|---|---|---|---|
| 4,801,452 | 1/1989 | Hunter et al. | 424/94.63 |
| 4,873,083 | 10/1989 | Hunter et al. | 424/83 |
| 4,879,109 | 11/1989 | Hunter | 424/83 |
| 5,017,370 | 5/1991 | Hunter et al. | 424/83 |
| 5,030,448 | 7/1991 | Hunter | 424/83 |
| 5,041,288 | 8/1991 | Hunter | 424/83 |
| 5,047,236 | 9/1991 | Hunter et al. | 424/83 |
| 5,547,667 | 8/1996 | Angelucci et al. | 424/181.1 |

OTHER PUBLICATIONS

A. V. Kabanov and V. P. Chekhonin, Polymeric Surfactant Micelles as Microcontainers for Neuroleptic targeting in the Brain, *J. Neuroimmunol.* (Suppl 1): 130 (1991).
A. V. Kabanov and V. Yu. Alakhov, *J. Controlled Release*, 28 (1994) 15–35.
Mortensen and Pedersen, *Macromolecules* (1993), 26:805–812.
Linse, *Macromolecules* (1993), 26:4437–4449.
Mortensen and Brown, *Macromolecules* (1993), 26:4128–4135.
Schillen et al., *Macromolecules* (1994), 27:4825–4832.
Schillen et al., *Macromolecules* (1993), 26:3611–3614.
Linse, *Macromolecules* (1994), 27:2685–2693.
Zhou and Chu, *Macromolecules* (1994), 27:2025–2033.
Zhou and Chu, *Journal of Colloid and Interface Science* (1988), 126:171–180.
Zhou and Chu, *Macromolecules* (1988), 21:2548–2554.
Alexandridis, *Macromolecules* (1994), 27:2414–2425.
Alexandridis, *Langmuir* (1994), 10:2604–2612.
Hecht and Hoffman, *Langmuir* (1994), 10:86–91.
Schmolka, *Journal of the Am. Oil Chemists' Society* (1977), 54:110–116.
Wilhelm et al., *Macromolecules* (1991), 24:1033–1040.
Hoes et al., *J. Controlled Release* (1995), 2:205–213.
Duncan et al., *J. Controlled Release* (1989), 10:51–63.
Pratei et al., *Br. J. Cancer* (1985), 52:841–848.
Page and Alakhov, *Proc Ann Meet Am. Assoc Cancer Res* (1992), 33:A3302.
Summary of article in *Nikkei Weekly*, Feb. 1994.
Slepnev et al., *Biochemistry International*, (1992) 26:587–595.
Kabanov et al., *Biochemistry International*, (May, 1992) 26:1035–1042.
Kabanov et al., *FEBS Letters*, (Dec. 1989) 258:343–345.

Kabanov et al., *J. Controlled Release*, (1992) 22:141–158.
Chekhonin et al., *FEBS*, (1991) 287:149–152.
"Highlights of U.S. Patents," *Anti–Viral Agents Bulletin*, Dec. 1993.
Kabanov et al., *Sov. Sci. Rev. D. Physiochem. Biol.* (1992), 11:1–75.
Kabanov et al., "Increasing the Transforming Activity of Plasmid DNA . . . ," Plenum Publishing Corporation (1989), pp. 133–136.
Levashov et al., "Chemical Modification of Proteins (Enzymes) with Water Insoluble Reagents" (1984), pp. 295–297.
Levashov et al., "Translocation of Waterproofed Proteins (Enzymes) into Lysosymes"(1985).
Kabanov et al., *Collect. Czech. chem. Commun.* (1989), 54:835–837.
Kabanov et al., *FEBS Letters* (1989), 250:238–240.
Kabanov et al., *Biol. Memb.* (1989), 2:1769–1785.
Kabanov et al., *Protein Engineering* (1989), 3:39–42.
Martinek et al., *Biochemica et Biophysica Acta* (1989), 981:161–172.
Kabanov et al., *Biomedical Science* (1990), 1:33–36.
Alakhov et al., *Biotechnology & Applied Biochemistry* (1990), 12:94–98.
Severin et al., *Advances in Enzyme Regulation* (1990), pp. 417–430.
Kabanov et al., *Biomedical Science* (1990), 1:63–68.
Melik–Nubarov et al., "Immunotherapeutic Prospects of Infectious Diseases," Mashi and Lange., Eds., Springer–Verleg, Berlin (1990), pp. 385–388.

(List continued on next page.)

*Primary Examiner*—Elli Peselev
*Attorney, Agent, or Firm*—Mathews, Collins, Shepherd & Gould, P.A.

[57] ABSTRACT

The present invention is directed to certain block copolymers of alkylethers linked to biologically active agents. More specifically, the invention relates to a conjugate between a biologically active agent and a block copolymer comprising: a biologically active agent covalently linked to a polymer comprising an A-type linear polymeric segment of relatively hydrophilic character, the repeating units of which contribute an average Hansch-Leo fragmental constant of about −0.4 or less and have molecular weight contributions between about 30 and about 500 and a B-type linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each said polymeric segment comprise an ether linkage. These block copolymers, when covalently linked with biologically active agents, can stabilize such agents, facilitate their entry into cells, enhance transport across histohematic barriers and, where the target cell has developed mechanisms to reduce the cell's sensitivity to the agent, substantially overcome such resistance. Despite the covalent attachment of a large substituent, such linked agents retain substantial activity.

14 Claims, No Drawings

OTHER PUBLICATIONS

Kabanov et al., *Collect Czech. Chem. Commun.* (1990), 55:587–589.

Kabanov et al., *International Symposium on Virology, Immunology and Society*, Kozminov and Radavsky, Eds., UNESCO, Venice (1991), pp. 303–322.

Slepnev et al., *Bioconjugate Chem.* (1992), 3:273–274.

Kabanov, *International Conference on Pharmaceutical Ingredients and Intermediates*, Published by Manufacturing Chemists (1992), pp. 89–96.

Melik–Nubarov et al., *Biochem. Molec. Biol. Int'l.* (1993), 29:939–947.

Kabanov et al., *Bioconjugate Chemistry* (1993), 4:448–454.

Sukhishvili et al., *Polymer Science* (1993), 35:1602–1606.

Kabanov and Alakhov, *Sixth International Symposium on Recent Advances in Drug Delivery Systems* (1993), pp. 73–76.

Kabanov and Alakhov, *J. Controlled Release* (1994), 28:15–35.

Kabanov et al., *FEBS Letters* (1990), 259:327–330.

Kabanov et al., *Biopolymers* (1994), 34:1437–1443.

Kabanov et al., *Polymer Preprints* (1991), 32:592–593.

Jones et al., *Bioconjugate Chem.* (1994), 5:390–399.

Wei, et al., *Bioconjugate Chem.* (1994), 5:464–478.

Yokoyama, *Critical Reviews in Therapeutic Drug Carrier Systems* (1992) 9(3,4):213–248.

Lin and Kawashima, *Pharm Actahelv* (1985), 60:339–344.

Yokoyama et al., *Cancer Research* (1991), 51:3229–3236.

Kataoka, *Proc. 2nd Tanigudi Conference on Polymer Research*, Ed. Yukio Imanishi, Kagahu–Dojun Press, Kyoto.

Yokoyama et al., *Cancer Research* (1990), 50:1693–1700.

Yokoyama et al., *Bioconjugate Chem.* (1992), 3:295–301.

Yokoyama et al., *J. Controlled Release* (1990), 11:269–278.

Kwon et al., *Langmuir* (1993), 9:945–949.

Yokoyama et al., *Biochemical and Biophysical Research Communications* (1989), 164:1234–1239.

Hatanaka, *Macromolecules* (1993), 26:1483–1485.

Kwon et al., *Pharmaceutical Research* (1993), 10:970–974.

Kabanov et al., *Enzyme Engineering 8, Annals of the New York Academy of Sciences* (1987) 501:63–66.

Geil et al., *Drug & Chemical Toxicology*, [JC:ed1] 15(1):15–31, 1992, Abstract.

Lee, *Pharm. Res.* (1993 Aug.) 10(8):1144–52, Abstract.

Kirillova et al., *Biotechnol. Appl. Biochem.* (1993 Dec.) 18 (Pt 3):329–39, Abstract.

Mokhova et al., *Biokhimiia* (1994 Jan.) 59(1):16–22, Abstract.

Kirillova, *Biotechnol. Appl. Biochem.* (1993 Dec.) 18 (Pt 3): 329–39, Abstract.

Teplova et al., *Biokhimiia*, (1993 Dec.) 58(12): 1929–35, Abstract.

Teplova et al., *Biokhimiia*, (1993 Nov.) 58(11): 1755–60, Abstract.

Efremova, *Biokhimiia*, (1993 Jul.) 58(7): 1071–6, Abstract.

Topchieva et al., *Biotechnol. Appl. Biochem.* (1993 Jun.) 17 (Pt 3): 337–48, Abstract.

POLYMER LINKED BIOLOGICAL AGENTS

The present invention is directed to certain block copolymers of alkylethers linked to biologically active agents. More specifically, the present invention relates to the discovery that certain block copolymers when covalently linked with biologically active agents can stabilize such agents, facilitate their entry into cells, enhance transport across histohematic barriers, enhance the potency of agents that interact with cell surface receptors and, where the target cell has developed mechanisms to reduce the cell's sensitivity to the agent, substantially overcome such resistance. Despite the covalent attachment of a large substituent, such linked agents can retain substantial activity.

Many drugs or other biological agents are difficult to deliver to the target tissue or organ because of undesirable biodistribution of these agents, their lability, poor membrane transport properties, and/or low efficacy of transport into target tissue or organ (which low net transport may be due to efficient, energy dependent export of the agent). Specifically, biological agents bind with serum proteins, and/or are imported by liver, other organs or white blood cells, leading to a decrease in effective concentration. Furthermore, metabolism of these agents can result in rapid clearance and in the formation of toxic metabolites that can cause side effects. In some cases the biological agents are not transported efficiently into the target tissues (e.g., cancer tumors), or cannot penetrate across histohematic barriers, such as the blood brain barrier, that isolate the target tissues or organs. In many cases the target cells develop mechanisms to reduce the cell sensitivity to the biological agents (e.g. multiple drug resistance), significantly decreasing the therapeutic effect of these agents.

Agents exhibiting such delivery problems are exemplified by many of the anti-neoplastic agents, including vinca alkaloids such as vincristine and vinblastine, mitomycin-type antibiotics such as mitomycin C and N-methyl mitomycin C, bleomycin-type antibiotics such as bleomycin $A_2$, antifolates such as methotrexate, aminopterin, and dideaza-tetrahydrofolic acid, colchicine, paclitaxel, anthracycline antibiotics and others. The anthracycline antibiotics exemplify drugs having delivery problems due to low stability, the development of drug resistance in the target tissue, or rapid metabolism. These antibiotics typically include a fused tetracycline aglycone ring system joined at the 7-position to daunosamine. They include, for instance, the compounds represented by the formula:

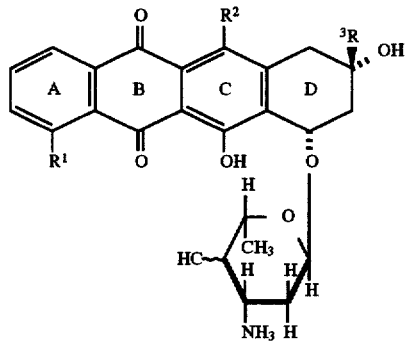

wherein $R^1$ is hydroxy or methoxy; $R^2$ is hydrogen or hydroxy; and $R^3$ is ethyl, acetyl, hydroxyacetyl, or an ester of hydroxyacetyl. These tetracycline antibiotics, like many anti-neoplastic agents, are believed to act by intercalating between the planar aromatic ring structures of DNA, thereby interfering with DNA replication. See, Neidle and Waring, *Molecular Aspects of Anti-Cancer Drug Action*, Pitman Press, 1983. Neoplastic cells are generally particularly susceptible, since they are actively replicating and thus synthesizing replica copies of their DNA.

A number of efforts to stabilize such drugs have been undertaken. For instance, Page and Alakhov, Proc. Ann. Meet. Am. Assoc. Cancer Res. (1992) 33: A3302, solubilize daunorubicin in a micellar solution of poly(oxyethylene)-poly(oxypropylene) to achieve a substantial increase in cytotoxicity against drug resistant transformed cells. Yokoyama et al. synthesized a conjugate between poly (ethyleneglycol)-poly(aspartic acid) block copolymer and multiple adriamycin molecules. *Cancer Res.* 51:3229–3296 (1991). In this work, doxorubicin molecules were attached by amide bonds to a number of the carboxylic acid groups of the copolymers. The conjugate was significantly less active on a mole doxorubicin basis versus the unconjugated drug. However, Yokoyama et al. concluded that the conjugate could be safely administered at doses where the free drug would be too toxic, and, at such elevated doses, was more effective in prolonging the survival of mice injected with tumors.

Other drug conjugates have been prepared in an effort to stabilize a drug. For instance, Pratesi et al. conjugated doxorubicin with poly-L-aspartic acid, each polymer of the conjugate attached to multiple doxorubicin molecules by ester bonds. *Br. J. Cancer,* 52:841–848, 1985. Hoes et al. coupled doxorubicin with poly- (α-L-glutamic acid) via various peptide linker/spacer groups. *J. Controlled Release,* 2:205–213, 1985. These authors reported a complex relationship between effectiveness and the type of linker used. Hoes et al. also emphasized the probable importance of carrier degradation in vitro to the appearance of doxorubicin activity. Duncan et al. reported linking doxorubicin to N-(2-hydroxypropyl)methyacrylamide copolymers via degradable and non-degradable linkers. *J. Controlled Release,* 10:51–63, 1989. The drug linked via degradable linker was effective, while that linked via non-degradable linker was devoid of activity.

The present invention relates to a class of covalent delivery vehicles that are structurally different from those discussed above. Conjugates with biologically active agents according to the invention have been found to retain effectiveness, to be stable in solution, to have effectiveness against cells that have been selected for drug-resistance that is essentially equal to their effectiveness against non-selected cells, and to remain in circulation for substantially longer periods than do the unmodified agents.

In one aspect, the invention relates to a drug or other biological agent delivery system. However, the invention can also be used to deliver a biological agent into a cell in vitro for diagnostic purposes. This purpose could include, for example, delivering an enzyme substrate capable of generating a fluorescent product into the cytoplasm of a cell. The enzyme activity in a cell can then be determined spectrophotometrically, and even used as a cell sorting criterion. The invention can also be used in cell culture to deliver an effector molecule such as a hormone that is necessary or facilitative for maintaining a given cell line in culture or for inhibiting the growth of a competing cell line.

The invention is described below with reference to the fragmental constants developed by Hansch and Leo. See Hansch and Leo, *Substituent Constants for Correlation Analysis in Chemistry and Biology,* Wiley, New York, 1979; James, *Solubility and Related Properties,* Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The invention relates to a conjugate between a biologically active agent and a block copolymer comprising:

a biologically active agent covalently linked to a block copolymer comprising an A-type linear polymeric segment of relatively hydrophilic character, the repeating units of which contribute an average Hansch-Leo fragmental constant of about −0.4 or less and have molecular weight contributions between about 30 and about 500 and a B-type linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each said polymeric segment comprise an ether linkage. In a preferred embodiment, the block copolymer comprises a polymer of formulas $$A-B-A', \quad (I)$$

$$A-B, \quad (II)$$

$$B-A-B', \quad (III)$$

or $$L(R^1)(R^2)(R^3)(R^4) \quad (IV)$$

wherein A and A' are A-type linear polymeric segments, wherein B and B' are B- type linear polymeric segments, and wherein $R^1$, $R^2$, $R^3$ and $R^4$ are either block copolymers of formulas (I), (II) or (III) or hydrogen and L is a linking group, with the proviso that no more than two of $R^1$, $R^2$, $R^3$ or $R^4$ shall be hydrogen.

Filed concurrently herewith was an application title "POLYNUCLEOTIDE COMPOSITIONS", Docket No. 313257-102, with Alexander Victorovich Kabanov, Valery Yulievich Alakhov and Sergey V. Vinogradov as named inventors. The entire disclosure of this application is incorporated herein by reference.

The degree of polymerization of the blocks of formulas (I), (II) or (III) can be between about 5 and about 400. Preferably, the degree of polymerization is between about 5 and about 200, more preferably, between about 5 and about 80. Preferably, the biologically active group is linked to at least one end group of the copolymers.

Biological agents are linked to the copolymers at one or more of the terminal ends. The repeating units that comprise the blocks will generally have molecular weight between about 30 and about 500, preferably between about 30 and about 100, more preferably between about 30 and about 60. Generally, in each of the blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages when A, A', B or B' is a carbohydrate. However, in one aspect, simple ether linkages are preferred.

Preferably, all of the repeating units that comprise blocks A or A' shall have a Hansch-Leo fragmental constant of less than about −0.4, more preferably, less than about −0.5, still more preferably, less than about −0.7. Preferably, all of the repeating units that comprise blocks B or B' shall have a Hansch-Leo fragmental constant of about −0.30 or more, more preferably about −0.20 or more.

The linkage between the biological agent and the block copolymers can be a direct linkage between a functional group at a terminal of the polymer and functional groups on the agent. Alternately, the linkage can be mediated by a bifunctional linking group X suitable for forming covalent attachments to a terminal groups of the polymer and a group on the agent. Since the linkages between repeating units of the polymer are predominately ether linkages, it will typically be the case that the terminal functionality of the polymer will be a hydroxide. Such hydroxides can be converted to aldehydes, ketones, amino groups, or carboxylic acids. When the biological agent is an anthracyline, the functional group that will be linked will typically be an amino group. Generally, the linking group X will have molecular weight of no more than about 300, more typically, no more than about 150. The linking group, in some instances, is still smaller. For instance, a terminal hydroxyl on the copolymer can be modified to create an oxycarbonyl ester. This terminal ester can then be reacted with an amino group from a biologically active group to form a —O—C(O)—NH— linkage, with the —C(O)— radical serving as the linking group.

Linker L will most typically be a α,ω-di-aminoalkyl group. However, any number of multifunctional linking groups may be utilized. Generally, linking group L will have molecular weight of no more than about 600, more typically, no more than about 300.

The copolymers of the present invention are exemplified by the block copolymers having the formulas:

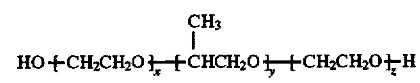

(V)

or, 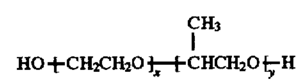 (VI)

or, 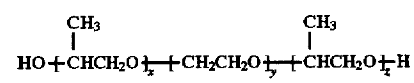 (VII)

or, (VIII)

in which x, y, z, i and j have values from about 5 to about 400, preferably from about 5 to about 200, more preferably from about 5 to about 80, and wherein for each $R^1$, $R^2$ pair, one shall be hydrogen and the other shall be a methyl group. Formulas (V) through (VII) are oversimplified in that, in practice, the orientation of the isopropylene radicals within the B block will be mixed. This mixed orientation is indicated in formula (VIII). Such poly(oxyethylene)-poly(oxypropylene) compounds have been described by Santon, *Am. Perfumer Cosmet.*, 72(4):54–58 (1958); Schmolka, *Loc. cit.* 82(7):25–30 (1967); *Non-ionic Surfactants*, Schick, ed. (Dekker, New York, 1967), pp. 300–371. A number of such compounds are commercially available under such generic trade names as "poloxamers," "pluronics" and "synperonics." Pluronic polymers within the B-A-B formula are often referred to as "reversed" pluronics, "pluronic R" or "meroxapol." The "polyoxamine" polymer of formula (VIII) is available from BASF (Wyandotte, MI) under the tradename Tetronic™. The order of the polyoxyethylene and polyoxypropylene blocks represented in formula (VIII) can be reversed, creating Tetronic R™, also available from BASF. See, Schmolka, *J. Am. Oil Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™. Polymers of the "Pluronic" type are known to be non-immunogenic and non-toxic.

The diamine-linked pluronic of formula (VIII) can also be a member of the family of diamine-linked polyoxyethylene-polyoxypropylene polymers of formula:

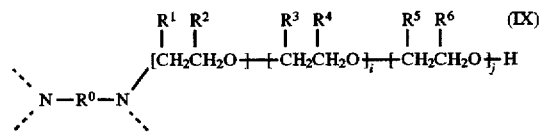

wherein the dashed lines represent symmetrical copies of the polyether extending off the second nitrogen. $R^0$ is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

Those of ordinary skill in the art will recognize, in light of the discussion herein, that even when the practice of the invention is confined to poly(oxyethylene)-poly(oxypropylene) block copolymers, the above exemplary formulas are too confining. An important feature of an A-type block is that the average Hansch-Leo fragmental constant of the repeating units in the block be about –0.4 or less. Thus, the units making up the block need not consist solely of ethylene oxide. Similarly, not all of the B-type block need be comprised solely of propylene oxide units. Instead, the blocks may incorporate repeating units other than those defined in formulas (V)–(VIII), so long as the general parameters of the A-type and B-type segments are maintained. Thus, in the simplest of examples, at least one of the repeating units in block A might be substituted with a side chain group.

In another aspect, the invention relates to a conjugate between a biologically active agent and a block copolymer of formula (I), (II), (III) or (IV), wherein the A and B-type blocks are substantially made up of repeating units of formula —O—R—$^5$, where $R^5$ is (1) —$(CH_2)_n$—$CH(R^6)$—, wherein n is an integer from 0 to about 5 and $R^6$ is hydrogen, cycloalkyl having 3–8 carbon atoms, alkyl having 1–6 carbon atoms, phenyl, alkylphenyl wherein the alkyl has 1–6 carbon atoms, hydroxy, hydroxyalkyl wherein the alkyl has 1–6 carbon atoms, alkoxy having 1–6 carbon atoms, alkylcarbonyl group having 2–7 carbon atoms, alkoxycarbonyl wherein the alkoxy has 1–6 carbon atoms, alkoxycarbonylalkyl wherein the alkoxy and alkyl each independently has 1–6 carbon atoms, alkylcarboxyalkyl wherein each alkyl group has 1–6 carbon atoms, aminoalkyl wherein the alkyl group has 1–6 carbon atoms, alkylamine or dialkylamino wherein each alkyl independently has 1–6 carbon atoms, mono- or di-alkylaminoalkyl wherein each alkyl independently has 1–6 carbon atoms, chloro, chloroalkyl wherein the alkyl has from 1–6 carbon atoms, fluoro, fluoroalkyl wherein the alkyl has from 1–6 carbon atoms, cyano, cyano alkyl wherein the alkyl has from 1–6 carbon atoms or carboxyl group, (2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents, or (3) a heterocyclic group, having 3–8 ring atoms, which can include heterocycloalkyl or heteroaromatic groups, which can include from 1 to 4 heteroatoms selected from the group consisting of oxygen, nitrogen, sulfur and mixtures thereto, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents.

Preferably, n is an integer from 1 to 3. The carbo cyclic or heterocyclic groups comprising $R^5$ preferably have 4–7 ring atoms, more preferably 5–6. Heterocycles preferably include 1–2 heteroatoms, more preferably, the heterocycles have one heteroatom. Those of ordinary skill will recognize that the monomers required to make these polymers are synthetically available. In some cases, polymerization of the monomers will require the use of suitable protective groups, as will be recognized by those of oridinary skill in the art. Preferably, the heterocycle is a carbohydrate or carbohydrate analog. Generally, the A and B-type blocks are at least about 80% comprised of —$OR^5$— repeating units, more preferably at least about 90%, yet more preferably at least about 95%.

In another aspect, the invention relates to a conjugate between a biologically active agent and a block copolymer of formulas (I), (II), (III) or (IV), wherein the A and B blocks consist essentially of repeating units of formula —O—$R^7$—, wherein $R^7$ is a $C_1$ to $C_6$ alkyl group. Generally, the A and B-type blocks are at least about 80% comprised of —$OR^5$— repeating units, more preferably at least about 90%, yet more preferably 95%.

The Hansch-Leo estimate of the octanol-water partitioning coefficient (P) for an organic molecule is calculated by the following formula:

$$\text{Log } P = \Sigma a_n f_n + \Sigma b_m F_m$$

where the $f_n$ values are the fragmental constants for the different groups in the molecule, the $a_n$ values are the number of any type of group in the molecule, the $F_m$ values are factors for certain molecular features such as single bonds or double bonds between groups for which fragmental constants have been assigned, and the $b_m$ values are the number of any such molecular feature. For instance, the Hansch-Leo fragmental constant for an ethylene oxide repeating unit (—$CH_2CH_2O$—) would be:

$$2f_C + 4f_H + f_O + (4-1)F_b = 2(0.20) + 4(0.23) + (-1.82) + 3(-0.12) = -0.86$$

The Hansch-Leo fragmental constant for a propylene oxide (—$CH_2CH_2(CH_3)O$—) repeating unit would be:

$$2f_c + F_{CH^3} + 3f_H \cdot f_O + (4-1)F_b = 2(0.2) + 0.89 + 3(0.23) + (-1.82) + 3(-0.12) = -0.2$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

While not wishing to be confined to theory, it is believed that one reason the conjugate of the present invention retains substantial biological activity is the flexibility of the ether linkages that are the predominate linker between the repeating units of the block copolymer of the invention. Because of the flexibility of the conjugate to the agent, it will have less tendency to block access of the agent to its intracellular site of action than would less flexible polymeric adducts, such as those reported by Hoes et al., *J. Controlled Release*, 2:205–213, 1985.

It is not critical to the present invention that the conjugate of the present invention be present in a micelle. Micelles are supramolecular complexes that form in aqueous solutions of certain amphipathic molecules due to the microphase separation of the nonpolar segments of the amphipathic molecules. Micelles form when the concentration of the amphipathic molecule reaches, for a given temperature, a critical micellar concentration ("CMC") that is characteristic of the amphipathic molecule.

The block copolymers utilized in the invention, when at a concentration above the CMC, will typically form micelles of from about 10 nm to about 100 nm in diameter. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks, and a hydrophilic shell formed by the A blocks. The micelles have translational and rotational freedom in solution, and solutions containing the micelles generally have low viscosity similar to that of water. Micelle formation typically occurs at concentrations from about 0.001 to 5% (w/v).

At high concentrations, some of the block copolymers utilized in the invention will form gels. These gels are viscous systems in which the translational and rotational freedom of the copolymer molecules is significantly constrained by a continuous network of interactions among copolymer units. In gels, microsegregation of the B block repeating units may or may not occur. To avoid the formation of gels, polymer concentrations will preferably be below about 15% (w/v), more preferably below about 10%, still more preferably below about 5%.

Due to the amphipathic character of the block copolymers of the conjugate, when the concentration of conjugate is sufficient, micelles will form. Under some circumstances, it is anticipated that the presence of micelles will be desirable. For instance, it may be desirable to incorporate an unconjugated agent, which agent can be the same or different from that conjugated to copolymer, in a micelles for coordinated administration with the conjugate. This approach would allow fine tuning of the pharmacokinetics and biodistribution of the agent. Drug dissolved in pluronic micelles would be expected to be more quickly available at the site of action.

However, it would not be expected to remain available over the substantially longer time periods over which the conjugate would remain available. Thus, in some instances, it can be desirable to have coadminister conjugate and unmodified bioactive agent, which may be dissolved in either conjugate or a mixture of conjugate and one or more block copolymer according to one of formulas (I), (II), (III) or (IV).

Biological agents in the conjugate or dissolved in block copolymer micelles have greater stability, resistance to degradative processes, resistance to nonspecific absorption and specific absorption onto carrier molecules such as bovine serum albumin, and resistance to uptake by liver and white blood cells. However, the micelle carriers generally will release over time the bioactive free form of the bioactive agent and to disaggregate from the micellar form when their concentration becomes low enough. The conjugate of the present invention provides a longer-term protective carrier.

While not wishing to be limited by theory, it is believed that when free or conjugated biological agent is in a micelle, a significant route of entry into cells will be through endocytosis. When not in a micelle, it is believed that entry is more direct. In either case, the hydrophobic portion of the conjugate is believed to facilitate cross-membrane transit of the conjugate, allowing the conjugate to encounter the cytoplasm of a target cell. In the case of an endocytosed micelle, while the micelle is "inside" the cell, it is still topologically isolated from the cytoplasm. However, it is believed that, in the harsh environment of the lysosomes into which endocytosed material will be transported, a portion of the copolymers conjugated to the bioactive agent will dissociate from the micelles, at which point the flexible hydrophobic moiety of the conjugate can facilitate transmembrane transport.

It will in some circumstances be desirable to incorporate the conjugate into micelles to allow for the noncovalent association of targeting molecules. See, for example, Kabanov et al., *J. Controlled Release*, 22:141 (1992). The targeting molecules that can be associated with the conjugate typically have a targeting group having affinity for a cellular site and a hydrophobic group. If the conjugate is formulated so that it will form micelles, by itself or in conjunction with other amphipathic molecules, the targeting molecule will spontaneously associate with the micelles and be "anchored" thereto through the hydrophobic group. These targeting molecules will typically comprise about 10% or less of the conjugate or block copolymer in a composition.

In the targeting molecule, the hydrophobic group can be among other things, a lipid group such as a fatty acid group. Alternately, it can be a block copolymer or other synthetic natural occurring polymer. The targeting group of the targeting molecule will frequently comprise an antibody, typically with specificity for a certain cell surface antigen. It could also be, for instance, a hormone having a specific interaction with a cell surface receptor, or a drug having a cell surface receptor. For example, glycolipids can serve as the targeting group to target a polysaccharide receptor.

In another embodiment of the invention, the targeting group can be attached to one end group of the copolymer, while the biological agent can be attached to one or more other end groups.

For polyethylene oxide-polypropylene oxide copolymer, the hydrophilic/hydrophobic properties, and micelle forming properties of a block copolymer are, to a certain degree, related to the value of a constant,n. The constant, n, is defined as:

$$n = (|B|/|A|) \times (b/a) = (|B|/|A|) \times 1.32$$

where |B| and |A| are the totals of the number of repeating units of polymerization of the hydrophobic and hydrophilic blocks of the copolymer, respectively, and b and a are the molecular weights for the respective repeating units. The value of n will typically be between about 0.2 and about 9.0, more preferably, between about 0.2 and about 1.5. Where mixtures of block copolymers are used, n will be the weighted average of n for each contributing copolymers, with the averaging based on the weight portions of the component copolymers. When copolymers other than polyethylene oxide-polypropylene oxide copolymers are used, similar approaches can be developed to relate the hydrophobic/hydrophilic properties of one member of the class of polymers to the properties of another member of the class.

Biologically Active Agents

Virtually any biologically active agent (also referred to herein as biological agent or bioactive agent), i.e., an agent that can act on a cell, organ or organism, including but not limited to drugs (pharmaceuticals) to create a change in the functioning of the cell, organ or organism, including but not limited to drugs (pharmaceuticals) can be used in the conjugate of the present invention. However, those that have low water solubility are particularly preferred. Such bioactive agents include but are not limited to anti-neoplastic agents such as paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin A$_2$, dideazatetrahydrofolic acid, aminopterin, methotrexate, cholchicine and cisplatin, antibacterial agents such as aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, antiparasitic compounds such as antimonials, proteins, peptides or polypeptides such as antibodies, toxins such as diphtheria toxin, peptide hormones, such as colony stimulating factor, and tumor necrosis factors, neuropeptides, growth hormone, erythropoietin, and thyroid hormone, neurotransmitters such as acetylcholine, lipoproteins such as alpha-lipoprotein, proteoglycans such as hyaluronic acid, glycoproteins such as gonadotropin hormone, immunomodulators or cytokines such as the interferons or interleukins, hormone receptors such as the estrogen receptor, non-steroidal anti-inflammatories such as indomethacin, salicylic acid acetate, ibuprofen, sulindac, piroxicam, and naproxen, antiglaucomic agents such as timolol or pilocarpine, anesthetics such as dibucaine, nucleic acids such as thymine, polynucleotides such as DNA or RNA polymers or synthetic oligonucleotides, which may be derivatized. The conjugate of the invention is anticipated to be particularly useful in increasing the activity of antisense DNA or RNA molecules. For the purpose of this application, enzymes are not biological agents. In one aspect of the invention, interferons will not be used as the biological agent.

Polynucleotides have been derivatized to facilitate entry into cells by covalently modifying the 5' or the 3' end of the polynucleic acid molecule with hydrophobic substituents. These modified nucleic acids generally gain access to the cells interior with greater efficiency. See, for example, Kabanov et al., *FEBS Lett.*, 259:327 (1990); Boutorin et al., *FEBS Lett.*, 23:1382–1390, 1989; Shea et al, *Nucleic Acids Res.*, 18:3777–3783, 1990. Additionally, the phosphate backbone of the polynucleotides has been modified to remove the negative charge (see, for example, Agris et al., *Boichemistry*, 25:6268 (1986); Cazenave and Helene in *Antisense Nucleic Acids and Proteins: Fundamentals and Applications*, Mol and Van der Krol, eds., p. 47 et seq., Marcel Dekker, New York, 1991) or the purine or pyrimidine bases have been modified (see, for example, *Antisense Nucleic Acids and Proteins: Fundamentals and Applications*, Mol and Van der Krol, eds., p. 47 et seq., Marcel Dekker, New York, 1991; Milligan et al. in *Gene Therapy For Neoplastic Diseases*, Huber and Laso, eds., p. 228 et seq., New York Academy of Sciences, New York, 1994). It is believed that the these modification techniques can be used in conjunction with the present invention of conjugating the polynucleotide to the block copolymers to increase the effect of the polynucleotide on target cells. When the invention is used with polynucleotides, it will often prove useful to neutralize the phosphate backbone of the polynucleotide with a hydrophobic cation such as N-[1-(2,3-dioleyloxy)-N,N-3'-methyammoniumchloride] or with a polycation. Polycations that present cationic groups with a spacing that matches the spacing of the phosphate groups on polynucleic acid are particularly preferred. For instance, the polycations with repeating unit —NH—CH$_2$CH$_2$CH$_2$— or repeating units comprising a mixture of —NH—CH$_2$CH$_2$CH$_2$— and —NH—CH$_2$CH$_2$CH$_2$CH$_2$— are particularly preferred.

The conjugate of the present invention is anticipated to more readily traverse the blood-brain barrier than does the corresponding free biological agent. Accordingly, a number of neuro-acting agents are anticipated to be useful as agents that can be conjugated according to the invention. These include, without limitation, neuroleptics such as the phenothiazines (for example compazine, thorazine, promazine, chlorpromazine, acepromazine, aminopromazine, perazine, prochlorperazine, trifluoperazine, and thioproperazine), rauwolfia alkaloids (for example, reserpine and deserpine), thioxanthenes (for example chlorprothixene and tiotixene), butyrophenones (for example haloperidol, moperone, trifluoperidol, timiperone, and droperidol), diphenylbutylpiperidines (for example pimozide), and benzamides (for example sulpiride and tiapride); tranquilizers such as glycerol derivatives (for example mephenesin and methocarbamol), propanediols (for example meprobamate), diphenylmethane derivatives (for example orphenadrine, benzotrapine, and hydroxyzine), and benzodiazepines (for example chlordiazepoxide and diazepam); hypnotics (for example zolpdem and butoctamide); beta-blockers (for example propranolol, acebutonol, metoprolol, and pindolol); antidepressants such as dibenzazepines (for example, imipramine), dibenzocycloheptenes (for example, amitriptyline), and the tetracyclics (for example, mianserine); MAO inhibitors (for example phenelzine, iproniazid, and selegeline); psychostimulants such as phenylethylamine derivatives (for example amphetamines, dexamphetamines, fenproporex, phentermine, amfeprramone, and pemoline) and dimethylaminoethanols (for example clofenciclan, cyprodenate, aminorex, and mazindol); GABA-mimetics (for example, progabide), alkaloids (for example co-dergocrine, dihydroergocristine, and vincamine); cholinergics (for example citicoline and physostigmine); vasodilators (for example pentoxifyline); and cerebro active agents (for example pyritinol and meclofenoxate).

The invention is particularly suited for stabilizing and delivering molecules that interact with a cell surface receptor. It has been observed that for such molecules the conjugate of the invention can be more effective than the unconjugated molecule, even in vitro where degradative processes are not anticipated to create substantial problems. While not wishing to be limited by theory, it is believed that this increase in effectiveness is due to the interaction of the B-type polymer block with cell membranes. Through this interaction, it is believed that the effective affinity constant of the effector for its receptor is increased substantially.

Preferred classes of biological agents include antineoplastic agents, antibacterial agents, antiparasitic agents, CNS agents, immunomodulators and cytokines, toxins, neuropeptides and polynucleotides. Biological agents, such as certain drugs for which target cells tend to develop resistance mechanisms are also preferred. Particularly preferred biological agents include anthracyclines such as doxorubicin, daunorubicin, or carminomycin, vinca alkaloids, mitomycin-type antibiotics, bleomycin-type antibiotics, flucanazol, amphotericin B, paclitaxel and derivatives, immunomodulators and cytokines such as interleukins and TNFs, erythropoietin, and polynucleotides, especially oligonucleotides.

For non-hormone biological agents, biological agents of molecular weight less than about 50,000 are preferred. More preferred are molecular weights less than about 40,000, still more preferred are molecular weights less than about 15,000. Biological agents that act by specifically interacting with a cellular molecule are preferred.

Biological Agent—Polymer Linkages

There are a large number of methods for linking biologically active agents to a block copolymer. Examples of such methods are outlined below. The methods often recite that a first linkable group, such as an amino or a hydroxyl group, is found at the terminal of the block copolymer, while a second linkable group is associated with the biologically active agent. Those of ordinary skill will recognize that in such cases the method generally can be adapted if the first linkable group is on the agent instead of the copolymer and the second is on the copolymer. Similarly, those of ordinary skill will recognize that a number of reactions recited below as applicable to linking a certain group can also be applied to strategies for linking other groups with related reactivities.

1. Reductive Alkylation—Linking Amino and Hydroxyl

Where the block copolymer terminates in one or more hydroxyl groups, these hydroxyl groups can be utilized to link the biologically active agent to the polymer. For instance, the terminal hydroxyls can be oxidized to an aldehydes. The aldehydes can then be reacted with amino groups that are substituents or adducts of the biologically active agent to form Schiff bases. These, in turn, can be readily reduced, preferably with sodium borohydrate to form a C-N linkage between polymer and biologically active agent. See Kabanov et al., *J. Controlled Release*, 22:141 (1992); *Meth Enzymol.*, XLVII, Hirs & Timasheff, Eds., Acad. Press, 1977.

2. Coupling Polymer and Agent Through an Acetyl Linkage

Where the block copolymer terminates in one or more hydroxyls, the hydroxyls can be reacted with bromoacetyl chlorides, forming bromoacetyl esters. The bromo groups can then be reacted with amino groups hat are substituents or adducts of biologically active agents, forming —N—CH$_2$—C(O)O—C— linkages. *Immobilized Enzymes*, Berezin et al., eds., MGU, Moscow, 1976.

3. Imidoester Linkages

Where the block copolymer terminates in a hydroxyl, it can again be converted to a bromoacetyl ester, as above. The bromoacetyl ester can be reacted with a cyanide salts forming a cyano intermediate. See, e.g., Sekiguchi et al., *J. Biochem.*, 85, 75 (1979; Tuengler et al., *Biochem. Biophys.*

*Acta*, 484, 1 (1977); Browne et al, *BBRC*, 67 126 (1975); and Hunter et al., *J.A.C.S.*, 84, 3491 (1962). The cyano intermediate can then be converted to an imido ester, for instance, by treatment with a solution of methanol and HCl. The imidoester can then be reacted with an amino group that is a substituent of or an adduct of a biologically active agent to create a —N—C(NH$_2^+$)CH$_2$C(O)O—C— linkage.

4. Linkage Formed Using 1,1'-carbonyl-bis-imidazole

A block copolymer terminating in at least one hydroxyl can be reacted with 1,1 '-carbonyl-bis-imidazole. The intermediate so formed can then be reacted with an amino group that is a substituent of or an adduct of a biologically active agent to form a —N—C(O)O—C— linkage. See Bartling et al., *Nature*, 243:342 (1973).

5. Linkage Using Cyclic Anhydrides

A block copolymer terminating in at least one hydroxyl can be reacted with e.g. succinic anhydride, to create a terminal carboxylic acid linked to the polymer via an ester bond. The acid group can be reacted with an amino group that is a substituent of or an adduct of a biologically active agent to form an amide bond. The amide formation can be directly mediated with a carbodiimide compound. Alternately, a reactive ester can be formed with the acid group and N-hydroxysuccinimide using a carbodiimide mediated reaction. The reactive ester will readily react with the amino group to form the amide. See, Means et al., *Chemical Modification of Proteins*, Holden-Day (1971).

6. Epoxide Mediated Linkages

A block copolymer terminating in at least one hydroxyl can be reacted with a bis epoxide compound such as 1,4-butanediol diglycidyl ether, to form a structure having a terminal epoxide function linked to the polymer by an ether bond. The terminal epoxide function is, in turn, reacted with an amino group that is a substituent of or an adduct of a biologically active agent to form a nitrogen-carbon linkage. Pitha et al., *Eur. J. Biochem.*, 94:11 (1979); Elling and Kula, *Biotech. Appl. Biochem.*, 13:354 (1991); Stark and Holmberg, *Biotech. Bioeng.*, 34:942 (1989).

7. Reductive Alkylation—linking amino groups.

This procedure relates to block copolymers terminating in at least one terminal amino group, such as the copolymer illustrated below:

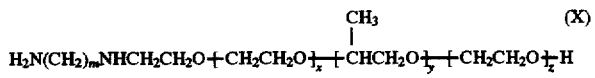

(X)

wherein m is an integer 1 to 25, and x, y and z are as defined above. The amino group may be alkylated by incubating with glutaraldehyde and a reducing agent such as sodium cyanoborohydride. This process will generate a terminal oxygen-containing group which may be an aldehyde or, if the second aldehyde group from glutaraldehyde was reduced in the first step, a hydroxyl group. If the terminal group is a hydroxyl group, it can be oxidized to an aldehyde group with an oxidant such as sodium iodate. This aldehyde functionality can be coupled with an amine group that is a substituent of or an adduct of a biologically active agent by reductive alkylation to form a —N—(CH$_2$)$_4$—N— linkage. Means and Feeney, *Biochemistry*, 7:2192 (1968).

8. Isothiocyanate-Mediated Coupling A block copolymer terminating in at least one amino group can be reacted with carbon disulfide in the presence of potassium hydroxide. Proprionyl chloride is then added to the reaction mixture. This reaction creates a terminal isothiocyanate group. The isothiocyanate group can then be reacted with an amino group that is a substituent of or an adduct of a biologically active agent to create a —N—C(S)—N— linkage. See Means et al., *Chemical Modification of Proteins*, Holden-Day (1971).

9. Phosgene-Mediated Linkage

A block copolymer terminating in at least one amino group can be treated with phosgene to create reactive intermediate. The intermediate can then be reacted with an amino group that is a substituent of or an adduct of a biologically active agent to yield a —N—C(O)—N— linkage. See Means et al., *Chemical Modification of Proteins*, Holden-Day (1971).

10. Dimethyl Adipimidate-Mediated Linkage

A block copolymer terminating in at least one amino group can be reacted with dimethyl adipimidate to create a reactive intermediate. The reactive intermediate can then be reacted with an amino group that is a substituent of or an adduct of a biologically active agent to create a —N—C(NH$_2^+$)—(CH$_2$)$_4$—C(NH$_2^+$)—N— linkage. See Lowe et al., *Affinity Chromatography*, Wiley & Sons, 1974.

11. 1,6-Diisocyanohexane-Mediated Linkage

A block copolymer terminating in at least one amino group can be reacted with 1,6-diisocyanohexane to create a reactive intermediate. The reactive intermediate can then be reacted with an amino group that is a substituent of or an adduct of a biologically active agent to form a —N—C(O)NH(CH$_2$)$_6$NHC(O)—N— linkage. See Means et al., *Chemical Modification of Proteins*, Holden-Day (1971).

12. The Technique of Kave et al.

The technique of Kaye et al., Nature, 216:514, 1967 can be used to create a

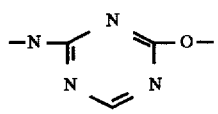

linkage between an amino group and a hydroxyl group.

The above reaction descriptions exemplify the large number of linkage strategies that can be employed to link a biologically active agent to the block copolymers of the invention. Other strategies will be apparent to those of ordinary skill in the art. Further general conjugation methods are described Means et al., *Chemical Modification of Proteins*, Holden-Day (1971); Glazer et al., *Chemical Modification of Proteins*, Elsevier, New York (1975); *Immunotechnology Catalog & Handbook*, Pierce Chemical Co.; *Polyethylene Glycol Derivatives*, Catalog, Shearwater Polymers, Inc. (1994).

The conjugate of the invention can be administered orally, topically, rectally, vaginally, by pulmonary route by use of an aerosol, or parenterally, i.e. intramuscularly, subcutaneously, intraperitoneallly or intravenously. The conjugate can be administered alone, or it can be combined with a pharmaceutically-acceptable carrier or excipient according to standard pharmaceutical practice. For the oral mode of administration, the conjugate can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the conjugate can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol.

The invention is further explained by reference to the following non-limiting examples. The examples make use of the following block copolymers of Formula III:

| Block Copolymer | x | y | z |
|---|---|---|---|
| Pluronic A | 25 | 38 | 25 |
| Pluronic B | 80 | 30 | 80 |
| Pluronic C | 150 | 56 | 150 |

EXAMPLE 1

Conjugate Synthesis

Tert-butylhypochlorite (300 μl) was added to 520 mg of Pluronic A dissolved in 15 mL of tert-butyl alcohol to initiate a reaction. The reaction was conducted at 20° C. in the dark for 20 hours. The precipitated intermediate that formed during the reaction was collected by filtration and dried under vacuum. The precipitate was dissolved in 5 mL isopropanol and heated in a water bath for two hours. The intermediate recovered after evaporating the solvent contained 1.15 aldehyde groups per polymer molecule. (The aldehyde content was determined using a dinitrophenylhydrazine assay.)

33 mg of the intermediate was dissolved in 1 ml of 0.05M borate buffer (pH 8.8 to 9.0). To this mixture was added 3.5 mg of daunorubicin and 25 mg of sodium cyanoborohydride to initiate a reductive alkylation reaction. The reaction mixture was stirred for 12 hours at 4° C. The polymeric products of the reaction were isolated by gel filtration chromatography on Sephadex LH-20, utilizing 90% aqueous isopropanol as the eluent. The isolated product contained 0.8 daunorubicin molecules per polymer molecule, as measured spectrophotometrically at 450 nm. Thin-layer chromatography confirmed the absence of any free daunorubicin in the polymeric product.

Similar conjugation efficiencies have been achieved using doxorubicin, carminomycin, 4'-epiadriamycin, 4-demethoxydaunomycin, 11-deoxydaunorubicin, 13-deoxydaunorubicin, adriamycin-14-benzoate, adriamycin-14-octanoate, and adriamycin-14-naphthaleneacetate in place of daunorubicin.

EXAMPLE 2

Conjugate Synthesis 1 g of Pluronic B was dissolved in 5 mL of dried benzene. Molecular sieves (0.3g, 3 Å pores), were added to the solution, which was allowed to stand over night to remove residual moisture. Approximately 3 to 4 g of dried sodium carbonate and 1.5 g of freshly recrystallized 2,4,6-tricholoro-1,3,5-triazine were then added to this dried solution to initiate a chlorination reaction. This reaction mixture was stirred for 24 hours. The solution was decanted from the molecular sieves and 20 mLs of hexane were added, resulting in the precipitation of a solid reactive intermediate. The solid was collected and dissolved in 2 mL of benzene. From this benzene solution, the reaction product was again precipitated by the addition of 10 mL of petroleum ether. This precipitation procedure was repeated four more times to remove unreacted 2,4,6-trychloro-1,3,5-triazine.

1 g of this reactive intermediate was dissolved in 1 mL of benzene. A solution of 0.5 g hexamethylenediamine (1,6-hexanediamine) dissolved in 1 mL of benzene was added to the dissolved intermediate to initiate a nucleophilic substitution reaction. This reaction mixture was allowed to stand at room temperature. After 12 hours of reaction, the polymer product was isolated from the reaction mixture by gel filtration on Sephadex LH-20, using isopropanol as the eluent. The polymeric second intermediate so isolated contained 0.3 amino groups per polymer molecule, as indicated by trinitrobenzenesulfonic acid titration. The absence of hexamethylenediamine was confirmed by thin-layer chromatography. 170 mg of this second intermediate were dissolved in 1 mL of 0.1M phosphate buffer (pH 7.0). This solution was mixed with 160 mL of a 25% aqueous solution of glutaraldehyde to initiate the formation of Schiff base linkages between the glutaraldehyde reactant and the polymer intermediate. This reaction mixture was stirred for 12 hours at room temperature. A polymeric third intermediate was isolated from this mixture by gel filtration chromatography on Sephadex LH-20, using 90% aqueous isopropanol as the eluent.

The isolated third intermediate (30 mg) was dissolved in 1 mL of 0.05M borate buffer (pH 8.8 to 9.0). To this solution were added 3 mg of daunorubicin and 20 mg of sodium cyanoborohydride, initiating a reductive alkylation reaction. The reaction mixture was stirred at 4° C. for 12 hours. The polymeric product from this reaction was isolated by gel filtration chromatography on LH-20 resin, using a 90% aqueous isopropanol solution as the eluent. The polymeric product contained 0.3 daunorubicin molecules per polymer molecule. The absence of free daunorubicin was confirmed by thin-layer chromatography.

EXAMPLE 3

Conjugate Synthesis

The procedures of Example 2 were used except that Pluronic C was used as the starting polymer and doxorubicin was used as the biologically active agent. The product contained 0.4 doxorubicin molecules per polymer molecule.

EXAMPLE 4

Solution Stability

The conjugate between daunorubicin and Pluronic A prepared in Example 1 ("conjugate A") was dissolved in sterile phosphate-buffered saline ("PBS") (pH 7.0) at a concentration of 0.2 µM. The concentration was calculated on the basis of the daunorubicin content of the conjugate. A corresponding 0.2 µM solution of free daunorubicin was prepared as a control. Both preparations were incubated at 37°, and the dissolved concentration of daunorubicin monitored by fluorescence spectrophotometry ($\lambda_{ex}$=485 nm). The results were as follows:

| Duration of incubation (hours) | $I_{485}$ (% of initial) Conjugate A | Control |
| --- | --- | --- |
| 0 | 100 | 100 |
| 6 | 103 | 92 |
| 27 | 100 | 89 |
| 43 | 97 | 68 |
| 78 | 98 | 54 |
| 120 | 100 | 37 |

EXAMPLE 5

Cytotoxicity Towards Agent Resistant Transformed Cells

Conjugate A was dissolved in RPMI 1640 medium (ICN Biomedicals Inc., Costa Mesa, Calif.) to a final concentration of 1%, and then the solution was filtered through a 0.22 µm filter to remove bacterial or fungal contamination. This conjugate A solution was used to make appropriate dilutions for the cell culture experiments described below. A comparable stock solution of unconjugated daunorubicin was also made.

The cytotoxicity studies utilized the SKOV3 line of transformed cells (hereinafter "SK cells") and the SKVLB cell line derived therefrom (hereinafter "SK-resistant cells"). The SK-resistant cell line is a multi-drug resistant transformed cell line derived from the SK cell line by long term cultivation in the presence of vinblastine.

Various dilutions of conjugate A or free daunorubicin were added to cell cultures cultured in RPMI 1630 medium supplemented with 10% fetal calf serum, at 37° C., and under a 5% $CO_2$ atmosphere. The cells were exposed to conjugate A or free daunorubicin for one hour. After this incubation, the cells were washed three times with fresh medium. Then, the cells were cultured under fresh medium for an additional four days.

The number of viable cells for each culture was determined by standard XTT analysis, which measures the activity of mitochondrial enzymes. See, Scudievo et al., *Cancer Res.*, 48:4827 (1988). $IC_{50}$ values (i.e., the concentration at which 50% inhibition was achieved) were determined by extrapolating from graphs plotting the number of viable cells versus the concentration of drug applied to the cells. The results were as follows:

| Sample | $IC_{50}$ (µg/mL)* SK | SK-resistant |
| --- | --- | --- |
| Conjugate A | 2.10 | 2.02 |
| Free daunorubicin | 0.32 | 2.55 |

*The concentration of free daunorubicin or of daunorubicin residues incorporated into the conjugate.

EXAMPLE 6

Cytotoxicity Towards Drug Resistant Transformed Cells

The conjugate between doxorubicin and Pluronic B prepared in Example 2 ("Conjugate B") was tested for cytotoxicity by the same methods outlines above for Example 5. The results were as follows:

| Sample | IC$_{50}$ (µg/mL) | |
|---|---|---|
| | SK | SK-resistant |
| Conjugate B | 37 | 27 |
| Free daunorubicin | 5.2 | 45 |

EXAMPLE 7

Cytotoxicity Towards Drug Resistant Transformed Cells

The cytotoxicity of Conjugate A was tested with respect to murine myeloma cell line Sp2/0 (hereinafter "Sp2") and a multi-drug resistant cell line derived therefrom by multiple passages in the presence of daunorubicin (the "Sp2-resistant cell line"). The site of toxicity was determined using the methods outlined in Example 5. The results were as follows:

| Sample | IC$_{50}$ (µg/mL) | |
|---|---|---|
| | Sp2 | Sp2-resistant |
| Conjugate A | 2.70 | 2.55 |
| Free daunorubicin | 0.22 | 2.60 |

EXAMPLE 8

Animal Toxicity

Conjugate A was injected intraperitoneally into C57B1/6 male mice at a variety of dose amounts. Ten animals were treated at each dose level. Corresponding toxicity experiments were done with unmodified daunorubicin. Animal survival was monitored daily for 14 days. From the data collected, maximum tolerated doses ("MTDs", the maximum dose that does not lead to death) and LD$_{50}$ values were calculated. The results were as follows:

| Sample | MTD (mg/kg)* | LD50 (mg/kg)* |
|---|---|---|
| Conjugate A | 112 | 280 |
| Control | 5.0 | 7.0 |

*Concentrations measured on the basis of daunorubicin content.

EXAMPLE 9

Tissue Distribution

Conjugate A* was prepared according to the protocol of Example 1 except that a tracer amount of [$^3$H]-labelled Pluronic A was incorporated into the conjugate. Various doses of Conjugate A* dissolved in phosphate-buffered saline, ("PBS") were injected intravenously into 7 week old C57B1/6 male mice (6 animals treated for each dose level, and for each time of treatment). The animals were sacrificed either at one hour or at 19 hours after injection. Tissue samples were collected and placed in 1 mL of tissue solubilizer (available from Serva, Germany) and homogenized in the cold. The homogenates were incubated for 14 hours at room temperatures, decolorized with 50 µL of 30% hydrogen peroxide, and incubated overnight at room temperature. The radioactivity in the samples was measured by liquid scintillation counting. The results were as follows:

| Organ | Drug Content (% of initial dose/organ ± SEM) | |
|---|---|---|
| | 1 hour | 19 hours |
| Blood | 72.3 ± 2.9 | 11.0 ± 1.2 |
| Liver | 4.8 ± 0.3 | 1.28 ± 0.43 |
| Kidney | 3.2 ± 0.2 | 0.84 ± 0.21 |
| Lung | 0.8 ± 0.1 | 0.27 ± 0.06 |
| Spleen | 1.2 ± 0.3 | 0.17 ± 0.07 |
| Heart | 0.2 ± 0.0 | 0.17 ± 0.02 |
| Brain | 0.9 ± 0.2 | 0.14 ± 0.01 |

EXAMPLE 10

Serum Levels Over Time

Either Conjugate A** (containing a tracer amount of [$^3$H]daunorubicin) or free [$^3$H]daunorubicin, was injected intraperitoneally into a number of 7 week old C57B1/6 male mice at a dose of 5 mg/kg body weight (based on daunorubicin content). At a given time, the animals in each treatment group were sacrificed and the amount of radioactivity in the blood determined. Twenty-four mice were used for each treatment group. The results were as follows:

| Time after drug administration | Drug in Plasma (cpm µl of blood) | |
|---|---|---|
| | Conjugate A | Daunorubicin |
| 5 min | 23 (± 3) | 431 (± 53) |
| 10 min | 42 (± 5) | 442 (± 58) |
| 30 min | 145 (± 17) | 360 (± 49) |
| 1 h | 276 (± 19) | 130 (± 22) |
| 3 h | 423 (± 39) | 60 (± 9) |
| 9 h | 568 (± 65) | 17 (± 5) |
| 15 h | 710 (± 68) | 0 |
| 20 h | 725 (± 76) | 0 |
| 30 h | 606 (± 53) | 0 |
| 40 h | 281 (± 31) | 0 |
| 55 h | 129 (± 16) | 0 |
| 75 h | 98 (± 11) | 0 |

EXAMPLE 11

Tumor Treatment

Six week old female Balb C mice were inoculated subcutaneously with 3×10$^6$ Sp2-resistant myeloma cells. Note that these cells, when injected into mice to create solid tumors, retain multi-drug resistance even 50 days after inoculation into the mice. Conjugate A or free daunorubicin was injected intravenously at 14, 18 and 22 days after tumor inoculation. The amount of conjugate A per and of free daunorubicin administered per injection was the MTD determined in Example 8. Tumor volumes were calculated by multiplying the long diameter of the tumor by the short diameter. The observed results were normalized by dividing the volume at a given day post-treatment (V) by the volume observed on the first day of treatment (V$_0$). The results were as follows:

| Days after first treatment | V/V₀ Conjugate A | Treated Control | Untreated Control |
|---|---|---|---|
| 0 | 1 | 1 | 1 |
| 3 | 1.5 | 2.7 | 2.5 |
| 6 | 2.1 | 3.4 | 3.2 |
| 8 | 2.9 | 5.1 | 5.5 |
| 10 | 4.2 | 6.6 | 8.4 |
| 13 | 5.6 | 11.6 | 12.1 |
| 16 | 8.6 | 20.9 | 18.6 |
| 20 | 10.1 | 25.9 | 25.6 |
| 23 | 13.8 | 38.4 | 32.8 |
| 27 | 17.1 | 50.9 | 42.4 |
| 31 | 16.9 | 68.3 | 45.5 |
| 34 | 18.2 | 73.0 | 61.4 |
| 38 | 19.4 | 83.4 | 73.4 |
| 42 | 21.1 | 113.8 | 100.6 |
| 45 | 20.5 | 111.9 | 123.6 |

EXAMPLE 12

Tumor Treatment

The same procedures outlined for Example 11 were utilized, except that the Sp2 myeloma cell line, which is not multi-drug resistant, was used. The results were as follows:

| Days after first treatment | V/V₀ Conjugate A | Treated Control | Untreated Control |
|---|---|---|---|
| 0 | 1 | 1 | 1 |
| 4 | 2.6 | 1.5 | 2.3 |
| 7 | 3.2 | 2.4 | 4.1 |
| 12 | 5.0 | 8.8 | 6.3 |
| 14 | 5.1 | 10.9 | 9.4 |
| 17 | 6.3 | 16.8 | 12.5 |
| 21 | 8.2 | 17.5 | 16.5 |
| 25 | 8.9 | 16.1 | 18.5 |
| 28 | 9.0 | 15.8 | 18.4 |
| 32 | 9.4 | 15.9 | 20.1 |
| 35 | 5.4 | 15.7 | 21.1 |
| 40 | 5.2 | — | — |
| 45 | 4.5 | — | — |

EXAMPLE 13

Compositions for I.P. Administration

Conjugate A (900 mg) and conjugate B were separately dissolved in 100 mL RPMI 1640. The solutions were heated for 30 minutes at 37° C., and then filtered through a 0.22 μm filter.

These compositions can be stored in the dark at room temperature for 7 days without substantial loss of cytotoxicity. Alternately, the compositions can be lyophilized and stored for at least 1 year in the dark at room temperature.

EXAMPLE 14

Composition Suitable for I.P. Administration

An ascorbate solution was prepared by dissolving 100 mg of sodium ascorbate and 100 mL of 9% sodium chloride. Conjugate B (500 mg) was dissolved in the ascorbate solution. The solution was incubated for 30 minutes at 37° C., and then filtered through a 0.22 μm filter. The composition was suitable for storage in the dark at room temperature for 7 days. Alternately, it can by lyophilized and stored for at least 1 year in the dark at room temperature.

EXAMPLE 15

Micellar Agent Delivery

Micelles were formed with a 1:1.5 (w/w) mixture of two polyoxyethylene-polyoxypropylene block copolymers of formula (I), wherein ratios (n) for the polymers were 1.00 and 1.50, respectively. These copolymers were formulated at 2.0% (w/v) in RPMI 1640 medium, and the mixture filter sterilized. To create a stock solution of a biological agent dissolved in the micelles of this formulation, daunorubicin was added to the copolymer solution.

The cytotoxicity of free daunorubicin and micelle dissolved daunorubicin was tested against (1) the MCF-7 line of human breast cancer cells, (2) the MCF-7AU line derived therefrom, which cell line is daunorubicin resistant but does not express the P-1 70 marker protein associated with some forms of drug resistance, and (3) the Dox-MCR-7, a MCF-7 derived cell line that is drug resistant and expresses the P-170 marker protein. The results were as follows:

| Daunorubicin conc. (ng/mL): | 50,000 | 10,000 | 2,000 | 400 | 80 | 16 |
|---|---|---|---|---|---|---|
| Cell line | % Inhibition | | | | | |
| Micelle formulation  MCF-7 | 100 | 100 | 84 | 65 | 42 | 12 |
| MCF-7AU | 100 | 100 | 100 | 96 | 69 | 39 |
| Dox-MCF-7 | 100 | 100 | 100 | 89 | 73 | 45 |
| Free drug  MCF-7 | 100 | 100 | 91 | 69 | 43 | 15 |
| MCF-7AU | 100 | 89 | 65 | 37 | 9 | 3 |
| Dox-MCF-7 | 100 | 86 | 62 | 39 | 7 | 2 |

EXAMPLE 16

Conjugate Synthesis with Oligonucleotide

A 12-mer oligonucleotide, 5'-CGTTCCTCCTGU ("Oligo A") complimentary to the splicing site (positions 983–994 on the viral genome) of the early mRNA of type 1 Herpes SimplexVirus ("HSV-1"), was synthesized using a 380B-02 DNA-synthesizer (Applied Biosystems, Calif.). The synthesizer used phosporamidite chemistry and an 8 min. synthesis cycle. Cycle conditions and preparation of the crude product were done as recommended by Applied Biosystems. The crude Oligo A obtained from the synthesis was precipitated from a 1M LiCI solution (0.5 ml) with acetone (2 ml). The precipitate was dissolved in triethylammonium acetate buffer and purified by reverse-phase high performance liquid chromatography on a Silasorb C18 column (9×250 mm, Gilson, France) developed with an acetonitrile gradient in a 20 mM TEM buffer (pH 8.5).

The 3'-terminal of the purified Oligo A was oxidized with periodate to create an aldehyde and conjugated by reductive alkylation with a hexamethylene-diamine linker, creating an amine derivative. See Che—Chung et al., Biochem. Internat., 25:767 (1991); Vinogradov et al., BBRC, 203:959 (1994). Pluronic A was similarly oxidized to create terminal aldehydes. The amine derivative (1 mg) was dissolved in 100 μl of 0.1M borate buffer (pH 9.0) and mixed with 2 mg of the Pluronic A derivative. 1.5 mg of sodium cyanoborohydride was added to the mixture to reduce the Schiff's bases formed between the amine and aldehyde groups. This reaction was allowed to proceed for 12 hours at 4° C. The polymeric product of this reaction was isolated by gel filtration chromatography on Sephadex LH-20, utilizing 90% aqueous isopropanol as the eluent. The conjugate so obtained is referred to hereinafter as "Oligo A Conjugate."

EXAMPLE 17

The Effect of Oligo A Conjugate on Virus Production

Oligo A and Oligo A Conjugate were separately dissolved in RPMI 1640 medium (ICN Biomedicals Inc., Costa Mesa, Calif.) to a final concentration of 0.2 mM (based on oligonucleotide absorbance). These stock solutions were then filtered through 0.22 μm filters to remove any possible bacterial or fungal contamination.

Monolayers of Vero cells were incubated for 1 hour at 37° C. in serum-free RPMI 1640 together with various concentrations of Oligo A or Oligo A Conjugate. The monolayers, while still exposed to oligonucleotides, were then infected with 1 plaque forming unit per cultured cell of HSV-1, strain L2 (from the Museum of Virus Strains of the D. I. Ivanovskii Institute of Virology, Russian Academy of Sciences, Russian Federation). This infection method has been described by Vinogradov et al. *BBRC*, 203:959 (1994). After 8 hours of exposure to virus and oligonucleotides, the medium on the cells was replaced with fresh medium containing 10% FCS. Medium from the cells was collected at 22 and 39 hours after the infective incubation, and the virus titer in the collected medium was determined as described in *Virology, A Practical Approach*, Mahy, Ed., IRL Press, Oxford Univ. Press, Washington, DC, 1985. The results were as follows:

| Sample | Oligonucleotide | Infectious Titer of HSV-1 (PFU/ml) | |
|---|---|---|---|
| concentration (mM) | concentration (μM) | 22 hours past infection | 39 hours past infection |
| Control (cells without oligonucleotides) | 0 | $5 \times 10^6$ | $1 \times 10^7$ |
| Oligo A | 10 | $3 \times 10^6$ | $5 \times 10^6$ |
| | 5 | $5 \times 10^6$ | $1 \times 10^7$ |
| | 2 | $5 \times 10^6$ | $1 \times 10^7$ |
| | 1 | $5 \times 10^6$ | $1 \times 10^7$ |
| Oligo A Conjugate | 10 | 0 | 0 |
| | 5 | 0 | $5 \times 10^2$ |
| | 2 | $1 \times 10^3$ | $7 \times 10^3$ |
| | 1 | $5 \times 10^4$ | $3 \times 10^6$ |

EXAMPLE 18

The Activity of Conjugated TNF α

Pluronic A (1 mg) that had been oxidized to create terminal aldehyde groups and 0.3 mg of human tumor necrosis factor α ("TNFα") (from ICN Biomedicals Inc., Costa Mesa, Calif.) were incubated together in 0.4 ml of 0.1M borate buffer (pH 9.0). The Schiff's bases that formed between the peptide hormone's amino groups and the aldehydes of Pluronic A were reduced by adding 0.6 mg of sodium cyanoborohydride and incubating for 12 hours at 37° C. See Kabanov et al., *J. Contr. Release*, 22: 141 (1992). The TNFα conjugate so obtained was isolated by gel filtration on Sephadex G-25 utilizing phosphate buffered saline, pH 7.0, as the eluent. The peptide-based concentration of the isolated conjugate and of comparative solutions of unconjugated TNFα were determined spectrophotometrically at 280 nm.

The specific activity of the conjugated and unconjugated TNFα with respect to SK cells were determined by XTT analysis of mitochondrial activity (see Example 5, above). The cells were exposed to various concentrations of conjugated or unconjugated TNFα for 24 hours. The cells were then washed three times with RPMI 1640 medium and analyzed by XTT analysis. The results were as follows:

| TNFα concentration, | Inhibition, % (± SD) | |
|---|---|---|
| (nM) | TNFα - Conjugate | TNFα |
| 0.01 | 9 (± 4) | 0 |
| 0.05 | 15 (± 5) | 2 (± 2) |
| 0.2 | 35 (± 6) | 5 (± 3) |
| 1.0 | 74 (± 9) | 4 (± 4) |
| 5 | 91 (± 11) | 10 (± 5) |
| 20 | 100 | 22 (± 5) |
| 50 | 100 | 35 (± 7) |
| 100 | 100 | 44 (± 6) |
| 200 | 100 | 80 (± 14) |

What is claimed is:

1. A conjugate between a biologically active agent and a block copolymer comprising a biologically active agent covalently linked to at least one end group of the block copolymer, wherein the block copolymer comprises
   (i) at least one polyether segment which is:
      (a) a homopolymer of the ethylene monomer —OCH₂CH₂— or
      (b) a copolymer or block copolymer of said ethyleneoxy monomer and the monomer —OCH(CH₃)CH₂—, each of said polyether segments having from about 5 to about 400 monomeric units.

2. The conjugate of claim 1 wherein the biologically active agent is at least one of an anthracycline, vinca alkaloid, mitomycin-type antibiotic, bleomycin-type antibiotic, fluconazol, amphotericin B, paclitaxel and derivatives thereof, immunomodulator, or cytokine, erythropoietin, or polynucleotide.

3. The conjugated biologically active agent of claim 1, wherein the biologically active agent is selected from the group consisting of doxorubicin, daunorubicin, carminomycin, fluconazol, amphotericin B, and mixtures thereof.

4. The conjugate according to claim 1 wherein each of said polyether segments has from about 5 to about 200 monomeric units.

5. The conjugate according to claim 1 wherein each of said polyether segments has from about 5 to about 80 monomeric units.

6. The conjugate according to claim 1 wherein said polyether segments have molecular weight between about 30 and about 500.

7. The conjugate according to claim 1 wherein said polyether segments have molecular weight between about 30 and about 100.

8. The conjugate according to claim 1 wherein said polyether segments have molecular weight between about 30 and about 60.

9. The conjugate according to claim 1 wherein said biologically active agent is directly linked to said block copolymer.

10. The conjugate according to claim 1 wherein said biologically active agent is linked to said block copolymer by a bifunctional linking group.

11. The conjugate according to claim 10 wherein the bifunctional linking group has a molecular weight of about 600.

12. The conjugate according to claim 10 wherein the bifunctional linking group has a molecular weight of about 300.

13. The conjugate according to claim 30 wherein the bifunctional linking group has a molecular weight of between about 150.

14. A conjugate between a biologically active agent and a block copolymer comprising a biologically active agent covalently linked to at least one end group of the block copolymer, wherein the block copolymer comprises at least one polyether segment, said polyether segment comprising repeating units of the formula —O—R—, wherein R is a $C_{1-6}$ alkyl group.

UNITED STATES PATENT AND TRADEMARK OFFICE
CERTIFICATE OF CORRECTION

PATENT NO. : 5,783,178
DATED : July 21, 1998
INVENTOR(S) : Kabanov, et al.

It is certified that error appears in the above-identified patent and that said Letters Patent is hereby corrected as shown below:

On the title page, item:

In the Inventors, item [75], should read "Alexander Victorovich Kabanov, Omaha, Nebraska, USA; Valery Yulievich Alakhov, Baie d'Urfe, Quebec, Canada In the Assignee, item [73], should read "Supratek Pharma Inc., Montreal, Quebec, Canada Signed and Sealed this Twenty-ninth Day of June, 1999

*Attest:*

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,783,178
DATED : July 21, 1998
INVENTOR(S) : Kabanov, et al.

It is certified that error appears in the above-identified patent and that said Letters Patent is hereby corrected as shown below:

In the claims, claim 13 should read "The composition of claim 10..."

Signed and Sealed this

Thirtieth Day of November, 1999

Attest:

Q. TODD DICKINSON

*Attesting Officer*        *Acting Commissioner of Patents and Trademarks*